United States Patent
Gray

(10) Patent No.: US 9,050,383 B2
(45) Date of Patent: Jun. 9, 2015

(54) SYSTEM AND METHOD FOR GENERATION OF ACTIVE SPECIES IN A MEDIA BY UV RADIATION

(71) Applicant: GOJO INDUSTRIES, INC., Akron, OH (US)

(72) Inventor: Robert L. Gray, Hudson, OH (US)

(73) Assignee: GOJO INDUSTRIES, INC., Akron, OH (US)

( * ) Notice: Subject to any disclaimer, the term of this patent is extended or adjusted under 35 U.S.C. 154(b) by 203 days.

(21) Appl. No.: 13/674,992

(22) Filed: Nov. 13, 2012

(65) Prior Publication Data
US 2013/0129567 A1  May 23, 2013

Related U.S. Application Data

(60) Provisional application No. 61/561,401, filed on Nov. 18, 2011.

(51) Int. Cl.
*A61L 2/22* (2006.01)
*A61L 2/18* (2006.01)
*A61L 2/20* (2006.01)
*A61L 2/00* (2006.01)
*A61L 2/10* (2006.01)

(52) U.S. Cl.
CPC ... *A61L 2/18* (2013.01); *A61L 2/20* (2013.01); *A61L 2/22* (2013.01); *A61L 2/0047* (2013.01); *A61L 2/10* (2013.01)

(58) Field of Classification Search
CPC .................................... A61L 2/22; A61L 2/10
USPC .......................................................... 422/29
See application file for complete search history.

(56) References Cited

U.S. PATENT DOCUMENTS

| | | | |
|---|---|---|---|
| 4,289,728 A | 9/1981 | Peel et al. | 422/24 |
| 4,366,125 A | 12/1982 | Kodera et al. | 422/295 |
| 4,643,876 A | 2/1987 | Jacobs et al. | 422/23 |
| 4,877,964 A * | 10/1989 | Tanaka et al. | 250/455.11 |
| 5,152,457 A * | 10/1992 | Burwell et al. | 239/102.2 |
| 5,221,520 A | 6/1993 | Cornwell | 422/122 |
| 5,751,007 A * | 5/1998 | Weaver | 250/504 R |
| 5,925,885 A | 7/1999 | Clark et al. | 250/492.1 |
| 6,534,075 B1 | 3/2003 | Hei et al. | 424/405 |

(Continued)

FOREIGN PATENT DOCUMENTS

| | | | |
|---|---|---|---|
| EP | 2 127 684 A1 | 12/2009 | A61L 2/10 |
| JP | 2004275330 A | 10/2004 | A23L 3/3418 |

OTHER PUBLICATIONS

International Search Report mailed Mar. 13, 2013 in corresponding application PCT/US2012/064756.

(Continued)

*Primary Examiner* — Sean E Conley
*Assistant Examiner* — Donald Spamer
(74) *Attorney, Agent, or Firm* — Renner Kenner Greive Bobak Taylor & Weber

(57) ABSTRACT

A system for sanitizing an article includes an ultraviolet light emitting a wavelength of light anywhere between 122-230 nm projected toward the article. A medium dispersed about the article and intersecting with the projected ultraviolet light is also provided. The medium interacts with the frequency of light to generate reactive oxygen species that eliminate microbes on the article. Specific light wavelengths may be used in combination with different mediums.

16 Claims, 1 Drawing Sheet

(56) References Cited

U.S. PATENT DOCUMENTS

| | | | |
|---|---|---|---|
| 6,960,321 B1 | 11/2005 | Ludwig | 422/26 |
| 6,967,787 B2 | 11/2005 | Makii et al. | 359/696 |
| 2002/0015697 A1 | 2/2002 | Beckman et al. | 424/94.4 |
| 2002/0155027 A1 | 10/2002 | Gutman | 422/29 |
| 2003/0086821 A1* | 5/2003 | Matthews | 422/29 |
| 2005/0211635 A1 | 9/2005 | Yeh et al. | 210/732 |
| 2008/0234786 A1 | 9/2008 | Cumbie | 607/88 |
| 2008/0255498 A1 | 10/2008 | Houle | 604/20 |
| 2009/0236215 A1* | 9/2009 | Burlica et al. | 204/164 |
| 2010/0028201 A1 | 2/2010 | Neister | 422/24 |
| 2010/0047138 A1 | 2/2010 | Snijkers-Hendrickx et al. | 422/186.3 |
| 2011/0272595 A1 | 11/2011 | Neister | 250/435 |

OTHER PUBLICATIONS

Written Opinion mailed Mar. 13, 2013 in corresponding application PCT/US2012/064756.

*Near-ultraviolet and blue spectral observations of sprites in the 320-460 nm region: N2 (2PG) emissions*; Heavner et al.; Journal of Geophysical Research; vol. 115; A00E44; doi: 10.1029/2009JA014858; 2010.

\* cited by examiner

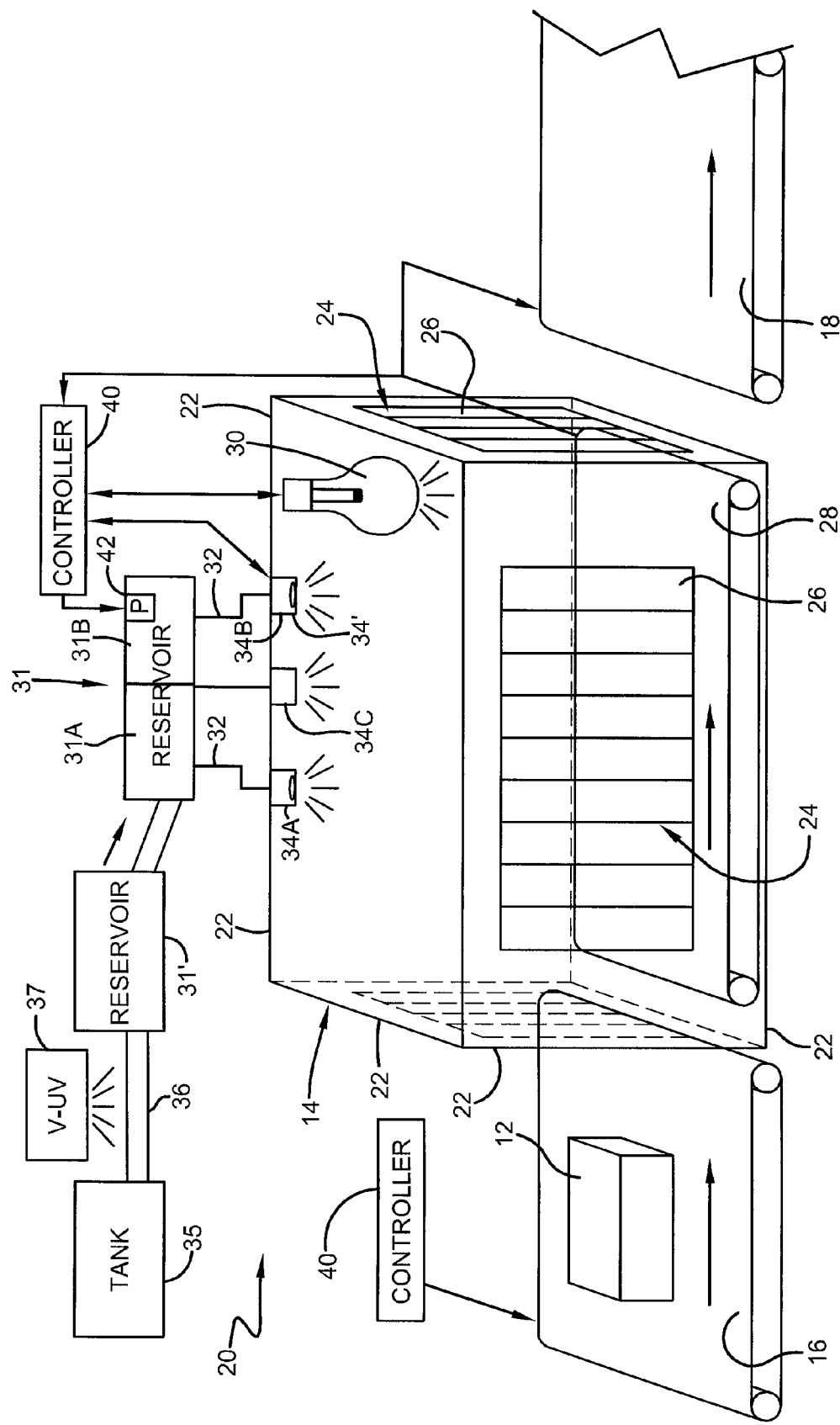

SYSTEM AND METHOD FOR GENERATION OF ACTIVE SPECIES IN A MEDIA BY UV RADIATION

CROSS-REFERENCE TO RELATED APPLICATION

This application claims priority of U.S. Provisional Application Ser. No. 61/561,401 filed Nov. 18, 2011, which is incorporated herein by reference.

TECHNICAL FIELD

Generally, the present invention is directed to a sanitization system. In particular, the present invention is directed to a sanitization system which produces reactive species capable of killing harmful microbes. Specifically, the present invention is directed to a sanitization system and related methods that use selected Vacuum UV (VUV) and/or Far UV (FUV) light frequencies in combination with a liquid media and optionally, with selected gases to produce highly efficacious anti-microbial activity.

BACKGROUND ART

It is well known in the art to utilize soap and water to effectively kill or reduce germs on a person's hand or other items to be cleansed. Minimizing germs is critical in hospital and food preparation settings so as to minimize the spread of disease and other harmful pathogens. This is done to ensure the well-being of patients and customers and to prevent further transmission of the germs.

However, as microbes and germs become more resistant to conventional methods of sanitization, other microbe/germ killing techniques have been developed. Indeed, use of some light frequencies in the ultraviolet range have shown promise. One common approach is to use UVC wavelengths (peak=254 nm) of UV light. However, the use of UVC light above 250 nm has drawbacks in that prolonged exposure can cause degradation to a person's skin or the material. As is well documented, these longer light wavelengths (250 nm and above) can cause burning which may contribute to formation of skin cancer or other maladies. Exposure to UVC wavelengths is also reported to directly damage DNA. The relatively long wavelength of UVC (vs. VUV and FUV<230 nm) allows penetration into the basil skin cells which are particularly sensitive to UV induced DNA damage.

Use of FUV for sanitization has been previously reported however, its efficacy is limited by lack of penetration which necessitates a direct line of sight by the UV rays. In other words, its inability to penetrate a skin wrinkle or fold allows microbes to be shielded from the ultraviolet rays and, as such, the effectiveness of the ultraviolet light is diminished in killing all microbes on the object.

It is also known to sometimes use peroxide in combination with UV light, but the peroxide has inadequate efficacy at concentrations which do not cause skin irritation. Further transportation, storage stability, and handling of peroxide are a complication for wide scale implementation in uncontrolled environments.

Direct disinfection of water by VUV has been reported. In such a scenario, a supply of water is routed through exposure of VUV light so as to generate a high level of active species in the water. But useful conversion of a liquid media in to a sanitizing liquid in combination with VUV and/or FUV is unknown.

Therefore, there is a need in the art for a sanitization system that uses select combination of ultraviolet light frequencies and a medium that increases both the number and reactivity of active species. Moreover, there is a need in the art to utilize a wavelength of ultraviolet light that does not damage the item being cleansed and which uses a medium that does not damage or degrade the article.

SUMMARY OF THE INVENTION

In light of the foregoing, it is a first aspect of the present invention to provide a system and method for generation of active species in a media by UV radiation.

It is another aspect of the present invention to provide a system for sanitizing an article, comprising an ultraviolet light emitting a wavelength of light anywhere between 122-230 nm projected toward the article, and a medium dispersed about the article and intersecting with the projected ultraviolet light, wherein the medium interacts with the frequency of light to generate reactive oxygen species that eliminate microbes on the article.

Yet another aspect of the present invention is to provide a method for sanitizing an article, comprising projecting an ultraviolet light having a wavelength of light anywhere between 122-230 nm toward an article, and disposing a medium about the article and the ultraviolet light, wherein the medium and the ultraviolet light mix so as to generate reactive oxygen species that come in contact with and kill microbes on the article.

BRIEF DESCRIPTION OF THE DRAWINGS

This and other features and advantages of the present invention will become better understood with regard to the following description, appended claims, and accompanying drawings wherein:

FIG. 1 is a schematic diagram of a system for sanitizing an article according to the concepts of the present invention.

DETAILED DESCRIPTION OF THE INVENTION

Referring now to FIG. 1, it can be seen that a system for sanitizing an article is designated generally by the numeral 10. An article 12, which may be any object that needs to be sanitized, is placed within the system 10 for cleaning. It will be appreciated that the article 12 may be any medical instrument; utensil; plate; food preparation device; surface, including animal or human skin surfaces such as hands, feet and the like; clothes; toys and any other object that is frequently exposed to germ-infested environments.

The system 10 includes a chamber 14 which receives the article 12 by manual insertion or by an automated system. In particular, an entry conveyor 16 may be placed on one side of the chamber 14 wherein a conveyor may be motorized or otherwise operated to move the article from one position to an entry position of the chamber. Positioned on the opposite side of the chamber 14 is an exit conveyor 18 which may also be motorized to move the article away from the chamber. The chamber 14 includes any number of chamber panels 20 such as a top, sides, front and/or back side so as to provide for a chamber that is at least partially enclosed. The chamber panels 20 may provide chamber openings in any one of the panels so as to allow for entry and/or exit of the article 12. The chamber openings 24 may be covered by deflectable slats 26 which cover the opening so as to maintain the enclosed environment while still allowing entry and egress of the article. The chamber may be sized to receive the size of the article 12.

An internal conveyor 28 may be provided within the chamber 14. The conveyor 28 is interposed between the conveyor entry 16 and the conveyor exit 18 so as to allow for transport of the article 12 through the chamber in a continuous fashion. The conveyors 16, 18 and 28 may be motorized or manually operated.

Maintained anywhere within the chamber 14 is an ultraviolet (UV) light source 30. Although only one light source is shown in the drawing, skilled artisans will appreciate that the "light source" may utilize multiple light sources strategically located within the chamber 14. The light source 30 may generate selected frequency wavelengths. In the present embodiment, the light source 30 generates light wave wavelength ranges between 122 to 230 nanometers. In other embodiments the range may be more focused, such as between about 180 to about 195 nanometers. And in other embodiments, a specific wavelength of about 188 nanometers can be utilized. In most embodiments, narrow ranges of ultraviolet light wavelengths such as ±one nanometer can be utilized. It will further be appreciated that if multiple light sources are used, the same or different frequencies as set out above could be used for each specific light source. For example, one light source may provide a specific wave length of 188 nanometers, while another of the light sources may provide a broader range of, wavelengths such as between 122 to 230 nanometers.

A reservoir 31 is associated with or positioned outside of the chamber 14 but in close proximity thereto. The reservoir 31 holds a "medium" such as air, water, nitrogen, hydrogen peroxide, and the like in various concentrations. In some embodiments, the reservoir may have separated compartments that contain different types of mediums. For example, reservoir 31A may contain air, while reservoir 31B may contain nitrogen. Each reservoir is associated with a feed line 32 which has a nozzle 34A/B at an opposite end wherein each nozzle delivers the selected medium to within the enclosure of the chamber 14. Skilled artisans will appreciate that the nozzles 34 may be configured to deliver the medium in the form of a stream, a spray, a mist or in any manner so as to widely disperse the medium into the chamber 14. This can be done by adjusting the size of the nozzle's outlet. The nozzle 34 may also incorporate a piezoelectric device 34' which generates droplets of the medium at pico-level sizes. Indeed, the droplets may be referred to as "atomized." These smaller droplets allow for generation of more active species which in turn greatly improves the cleaning effectiveness of the system 10. The nozzles may be positioned relative to the light source(s). In other words, in some embodiments the nozzles may be positioned below the light source and in other embodiments the nozzles are positioned above and around the light source.

In an alternative embodiment, a supplemental reservoir 31' may be associated outside of the chamber. The reservoir 31' may disperse a medium directly into the chamber 14 or into one of the reservoirs 31A/31B and then into the chamber 14. The supplemental reservoir may hold a fluid, such as water, that has recently been treated. For example, the fluid can be held in a tank 35 which allows the fluid to flow through an appropriately-sized pipe or trough 36 that is exposed to vacuum UV frequency light generated by a vacuum UV light source 37. Exposure to the vacuum UV light generates a higher level of active species, where the treated fluid can be further treated within the chamber 14 as will be discussed.

A controller 40 is connected to the UV light source 30, the reservoirs 31A/B, the piezoelectric nozzle 34' and to the conveyors 16, 18 and 28. The controller 40, upon receiving input from a technician or user, controls the operation of the light, the delivery of the medium to within the enclosure, the atomization of the medium and the transport of the article through the chamber as needed. Skilled artisans will appreciate that a pumping mechanism 42 may be associated with each of the reservoirs so as to deliver the medium at a desired rate to the confines of the chamber 14.

In operation, the article 12 is transported through the chamber 14 by the conveyors 16, 18 and 28 wherein the article enters the opening through the deflectable slats and is either stopped for a period of time or is continually transported through the enclosure at a predetermined rate so as to be exposed to both the medium and the ultraviolet light rays while they interact with one another. In the alternative, the article may be manually inserted through the deflectable slats and exposed for a predetermined or adequate period of time. Exposure may consist of rotating and/or moving the article to ensure every surface is exposed to a combination of the light and the medium. Generally, the system 10 utilizes the ultraviolet light and the medium to deactivate pathogens on surfaces of the article or on the user's skin. In one embodiment, far ultraviolet light is used (122 to 230 nm) to generate selected species, such as nitric oxide, hydroxyl radicals, and singlet oxygen which in turn provides highly efficacious antimicrobial activity toward surface dwelling microbes. The medium may be selected from any gas type, such as oxygen, air and nitrogen, which allows for modification of the available energy at the article's substrate surface of the article as well as determining the type of active species available. It is believed that selection of a specific ultraviolet frequency and the selection of a specific medium allows tuning of the system for efficacy and safety of the substrate. In other words, depending upon the particular substrate, the surface characteristics of the substrate, the concentration of a medium, such as nitrogen, and particular wavelength of light, such as 188 nm, is well suited to kill selected pathogens without causing damage to the article or skin. Moreover, skilled artisans will appreciate that the features' processes and attributes of the system 10 disclosed herein may be used in permutation or combination to effectively sanitize an article.

Skilled artisans will appreciate that the above described system and methodology generates reactive species in air or oxygen, or directly in a water and/or alcohol solution to create a coating which contains effective concentrations of active species that reduces or kills unwanted microbes. In some embodiments, a water and/or alcohol medium could be sprayed or misted between the ultraviolet light source and the substrate of the article. In other embodiments, a pre-treated medium, such as the vacuum-UV exposed fluid held in reservoir 31' could be utilized. And in other embodiments, the use of dry nitrogen gas medium is believed to increase the total energy of a surface by eliminating oxygen and water absorption of the ultraviolet radiation. Such configurations are believed to be advantageous in that the combination of high energy from the UV light and low skin penetration can be expected to create a fast kill zone at the uppermost layer of skin or the article without affecting the live skin cells below the surface. Generation and use of nitric oxide (a known antimicrobial) in the chamber 14 would also be highly efficacious and advantageous in sanitizing the article. The use of a liquid medium allows for sanitization to occur in areas without direct line of sight to the ultraviolet light, which is a current limitation of UV sanitizing systems. Use of an alcohol media produces additional efficacy beyond the ultraviolet light itself wherein the UV contribution broadens the spectrum of the microbe kill. The system and related methods are believed to be more effective at sanitizing objects. For example, sterilization in hospital settings currently can take up to ten minutes. However, use of the disclosed system and methods is believed to provide an equivalent or better sanitization in significantly less time.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A system for sanitizing an article, comprising:
   an ultraviolet light emitting a wavelength of light anywhere between 122-230 nm projected toward the article;
   a partially enclosed chamber which carries said ultraviolet light;
   a medium dispersed about the article and intersecting with the projected ultraviolet light while in said partially enclosed chamber, wherein said medium comprises at least two substituents, one said substituent is nitrogen gas and the other said substituent is a liquid, and, wherein both said nitrogen gas and said liquid react with said ultraviolet light in said partially enclosed chamber to generate reactive species that eliminate microbes on the article; and
   a tank for holding said liquid substituent, said tank supplying said liquid substituent delivered to said partially enclosed chamber; and a vacuum UV light which emits a wavelength of ultraviolet light toward said liquid substituent prior to entering said partially enclosed chamber, wherein said liquid substituent is water pre-treated by exposure to light generated by the vacuum UV light.

2. The system according to claim 1, wherein said liquid is selected from the group consisting of water, alcohol, and a mixture of water and alcohol.

3. The system according to claim 1, wherein said wavelength of light is between 180-195 nm.

4. The system according to claim 1, wherein the liquid substituent is alcohol and said wavelength of light is 180 nm.

5. The system according to claim 1, wherein said wavelength of light is between 195-230 nm.

6. The system according to claim 1, further comprising:
   a nozzle to disperse said medium within said partially enclosed chamber.

7. The system according to claim 6, wherein said nozzle comprises a piezoelectric nozzle that atomizes said medium.

8. The system according to claim 1, wherein said medium is substantially nitrogen gas and said wavelength of light is 188 nanometers.

9. A method for sanitizing an article, comprising:
   providing a chamber having at least one opening to allow for entry and exit of the article;
   projecting an ultraviolet light having a wavelength of light anywhere between 122-230 nm toward an article in said chamber;
   disposing a medium about the article and said ultraviolet light while the article is in said chamber, wherein said medium comprises at least two substituents, one said substituent is nitrogen gas and the other said substituent is a liquid and wherein both said nitrogen gas and said liquid react with said ultraviolet light to generate reactive species that come in contact with and kill microbes on the article; and
   providing a tank for holding said liquid substituent; pre-treating said liquid substituent held in said tank by exposure to vacuum UV light before said liquid substituent is delivered to said partially enclosed chamber.

10. The method according to claim 9, further comprising:
    conveying the article through said chamber.

11. The method according to claim 9, further comprising:
    adjusting at least one of the wavelength of said ultraviolet light or a concentration of said medium to optimize kill effectiveness of selected microbes.

12. The method according to claim 9, further comprising:
    adjusting the wavelength of said ultraviolet light to between 180-195 nm.

13. The method according to claim 9, further comprising:
    providing said chamber with at least one opening covered by deflectable slats.

14. The method according to claim 9, further comprising:
    projecting an ultraviolet light wavelength of 188 nm toward the article.

15. The method according to claim 9, wherein disposing comprises:
    dispensing said medium through a nozzle so as to form droplets that are exposed to said ultraviolet light.

16. The method according to claim 15, wherein disposing comprises:
    dispensing said medium through a piezoelectric nozzle so as to form atomized droplets that are exposed to said ultraviolet light.

* * * * *